US006505499B1

(12) United States Patent
Hackworth et al.

(10) Patent No.: US 6,505,499 B1
(45) Date of Patent: Jan. 14, 2003

(54) PUNCTURE RESISTANCE IN ULTRA-THIN ALUMINUM PRESSURE VESSELS

(75) Inventors: Matthew R. Hackworth, Pearland, TX (US); John W. Cooley, Ballwin, MO (US); John M. Henshaw, Tulsa, OK (US); Randy Houchins, St. Louis, MO (US); Paul Siefken, O'Fallon, MO (US); Dwight Davis, Tulsa, OK (US)

(73) Assignee: Metal Container Corporation, St. Louis, MO (US)

( * ) Notice: Subject to any disclaimer, the term of this patent is extended or adjusted under 35 U.S.C. 154(b) by 0 days.

(21) Appl. No.: 09/821,890

(22) Filed: Mar. 30, 2001

Related U.S. Application Data

(60) Provisional application No. 60/193,596, filed on Mar. 30, 2000.

(51) Int. Cl.$^7$ .............................................. G01M 3/02
(52) U.S. Cl. ........................................ 73/12.09; 73/52
(58) Field of Search .................. 73/12.01, 12.04–12.07, 73/12.09, 12.11–12.14, 818, 821, 52, 838, 839

(56) References Cited

U.S. PATENT DOCUMENTS

| | | | | |
|---|---|---|---|---|
| 2,645,936 A | * | 7/1953 | Albrrecht | 73/821 |
| 4,555,935 A | * | 12/1985 | Elert | 73/52 |
| 4,721,000 A | | 1/1988 | Scanlon | 73/833 |
| 5,567,866 A | | 10/1996 | Popp | 73/11.09 |
| 5,616,857 A | | 4/1997 | Merck, Jr. et al. | 73/82 |
| 5,929,348 A | * | 7/1999 | Stein et al. | 73/12.07 |

OTHER PUBLICATIONS

*Drop and Puncture Testing of 1/4 Scale Model of NUPAC 125B Rail Cask*, M.M. Warrant and B.J. Joseph, Sandia National Laboratories, Albuquerque, NM 87185, pp 357–362, no date.

*Standards for High Pressure Cylinders for the On–Board Storage of Natural Gas as Fuel for Automotive Vehicles*; Joe Wong and Craig Webster, International Conference on Pressure Vessel Technology, vol. 2, ASME 1996; pp 287–292, Jul. 21–26, 1996.

*Static and Dynamic Penetration of Steel Tubes by Hemispherically Nosed Punches*; g. G. Corbett, et al. Int. J. Impact Engineering; vol. 9, No. 2, pp 165–190, Great Britain, 1990.

*On the Catastrophic Failure of High–Pressure Vessels by Projectile Impact*, Z. Rosenberg, et al., Int. J. Impact Engineering, vol. 15, No. 6, pp 827–831, Great Britain, Feb. 1994.

*Numerical Simulations of Fragment Impact on Liquid Filled Containers*, P.W. Randles, et al., PVP, vol. 361, Structures Under Extreme Loading Conditions, ASME 1998.

*Space Station Jem Design Implementation and Testing for Orbital Debris Protection*; Kuniaki Shiraki, et al., Int. J. Impact Engineering, vol. 20, pp 723–732, Great Britain, 1997.

*Spherical Missile Impact and Perforation of Filled Steel Tubes*; ma Xiaoping, et al., Int. J. Impact Engineering, vol. 3, No. 1, pp 1–16, Great Britain 1985.

(List continued on next page.)

Primary Examiner—Robert Raevis
(74) Attorney, Agent, or Firm—Storm & Hemingway, L.L.P.

(57) ABSTRACT

An apparatus and method for measuring the puncture resistance of an aluminum can that has improved repeatability and more accurately simulates end-use punctures. A penetrator that moves in a horizontal direction and is driven by a falling weight impacts a pressurized aluminum can containing liquid. The aluminum can is impacted by a penetrator of the puncture gauge in an area below the liquid level. Various sensors, such as a load cell and a displacement transducer, measure data from the impact and the data is compiled and analyzed by a data acquisition system.

55 Claims, 5 Drawing Sheets

OTHER PUBLICATIONS

*An Experimental Study on Puncture Resistance of Spent Fuel Shipping Cask by Drop Impact Tests*, I. Sakamoto, et al., 4$^{th}$ Proceedings of the International Symposium, Sep. 22–27, 1974, Miami Beach, Florida.

*Impact of Projectile on Elliptical Tank Head*, M. Lishan, et al., Advanced Technology and Research, Inc. pp 245–260, 1985.

*Risk Based Package Design*; Raymond A. Freeman, et al. Process Safety Progress, vol. 16, No. 1, Spring 1997, pp 14–17.

*Design of Radioactive Material Shipping Packaging for Low–Velocity Puncture Resistance*, R.E. Nickell, et al. Nuclear Engineering and Design 74, (1982), PP 223–232.

*Effect of Strength and Thickness on Notch Ductility*, J. H. Gross, Impact Testing of Metals, ASTM STP, 1970, pp 21–52.

*Procedures and Problems Associated with Reliable Control of the Instrumented Impact Test*; D. R. Ireland, Instrumental Impact Testing, ASTM STP 563, American Society for Testing and Materials, 1974, pp 3–29.

*Introduction to Impact Engineering*; M. Macaulay, Brunel University; pp 231–258, London, New York, Chapman and Hall.

*The Propagation of Mechanical Pulses in Anelastic Solids*; H. Holsky, Brown University, Providence, R.I., Winter Annual Meeting of the ASME, Chicago, IL, Nov. 09, 1965.

*Crack Initiation and Extension under Penetration of Thin Metal Sheet*; Kaminishi, et al., JSME International Journal, Series L, vol. 35, No. 4, 1992, pp 475–481.

*The Mechanics of Penetration of Projectiles Into Targets*; Backman, et al., International Journal of Engineering, vol. 16, pp 1–99. 1978.

*Fracture Mechanics of Aluminum Beverage Container Side-–Wall Rupture*; Matthew Roy Hackworth, A Thesis Approved for the Discipline of Mechanical Engineering, The University of Tulsa, The Graduate School, 1998.

*Damage in Composite Materials Due to Low Velocity Impact*; Longin B. Greszczuk, Impact Dynamics, pp 55–235.

*Properties of Pure Aluminum*; Aluminum, Properties and Physical Metallurgy, American Society for Metals, Metals Park Ohio, pp 1–133.

* cited by examiner

PUNCTURE RESISTANCE IN ULTRA-THIN ALUMINUM PRESSURE VESSELS

CROSS-REFERENCE

This application claims priority to prior provisional application serial No. 60/193,596, filed on Mar. 30, 2000.

TECHNICAL FIELD

The present invention relates generally to a method and apparatus for measuring puncture resistance in pressurized ultra-thin aluminum containers, and more particularly puncture resistance in aluminum containers for carbonated beverages.

BACKGROUND OF THE INVENTION

The invention relates to a method and apparatus for measuring resistance in pressurized aluminum containers. It is specifically related to an improved method and apparatus for measuring puncture resistance in aluminum cans containing carbonated beverages for the purpose of assessing the effect of engineering changes to the can on its ability to resist puncture and rupture failures.

The carbonated beverage industry, and particularly the soda and beer industries are familiar with the use of aluminum containers or cans for packaging of carbonated beverages. Aluminum cans are used primarily as containers for retail sale of beverages in individual portions. Annual sales of such cans are in the billions and consequently, over the years, their design has been refined to reduce cost and improve performance. Other refinements have been made for ecological purposes, to improve reclamation and promote recycling.

Aluminum cans are usually formed from thin sheets of aluminum alloy, such as the aluminum alloy 3004 or 3104. The interior of the can is spray coated after forming. The coating protects the aluminum in the interior of the can from the corrosive beverage products that the can is designed to hold, and conversely protects the beverage flavor from being altered due to contact with the aluminum can. The starting gauge of the aluminum coil is approximately 10.5 mils (0.0105 inches) thick before any can forming begins. The coil is blanked and cold worked to form a can body, consisting of a bottom portion and a generally cylindrical portion typically referred to as the sidewall, which are joined to a separately manufactured can lid or closure. The can forming process and general can design and dimensions are well known in the art and will not be discussed in detail. Each component of the can has certain specifications and requirements, which are also well known in the art. For instance, the upper surface of the can lids must be configured to nest with the lower surface of the can bottoms so that the cans can be easily stacked one on top of the other. Additionally, the cans must be capable of withstanding pressures of approximately 90 psi, once filled with carbonated beverage.

The aluminum can industry continues to develop new ways to improve can performance and reduce costs without sacrificing the ability to satisfy these functional requirements. Significant cost reductions in manufacturing aluminum cans may be realized in material savings, primarily through the use of thinner metal to form the cans. Optimization of can and lid geometry has permitted continued use of thinner metal materials without seriously impacting the ability to satisfactorily maintain functionality of the cans.

Although the use of thinner metal has its advantages and can be used while still meeting essential functional requirements, it also has its drawbacks. One of the drawbacks relates to decreased puncture and fracture resistance in the aluminum cans manufactured with thinner metal. The current typical manufacturing process for aluminum beverage cans optimizes the metal usage by drawing and ironing the sidewall of the can. This results in the can being thinner than the coil starting gauge in the can sidewall, known as the thinwall portion, which is approximately 0.004" thick. Thinner sidewalls in aluminum cans are more susceptible to being punctured by contact with an external surface and are more susceptible to fracture failure. The principles underlying failures of pressure vessels due to puncture and fracture are well known in the art and do not require further detailed discussion. Relevant principles related to puncture and fracture that are specific to aluminum beverage cans are discussed below.

Failures in aluminum beverage cans manifest as either a rupture or a leak, depending on various conditions. A fracture in an aluminum can results in failure of the can and may be caused by slow forces, such as fatigue or corrosion, or by a puncturing event. A puncturing event is generally a dynamic contact between a foreign, external surface and the container. Fracture resistance is generally considered a material property that quantifies a material's resistance to crack growth, while puncture resistance is a container property that quantifies the load, deflection and/or energy that a particular container is capable of withstanding before fracturing due to an impact with an external surface. A can fracture that grows rapidly is known as a rupture, where the can splits open and the contents, which are under pressure, are violently discharged. A fracture that does not result in a rupture is known as a leak, where the pressurized contents slowly leak out of the can. The tendency of a pressure vessel, such as a can, to rupture or leak in response to a fracture is described by the fracture mechanics design theory known as Leak-Before-Break.

Rupture failures in industrial pressure vessels are extremely dangerous and can cause death, injury and substantial damage. By comparison, damage caused by the rupture of aluminum beverage cans is less severe. The contents of the can, and in some rare occasions small pieces of the container itself, are projected into the local surroundings. Regardless of the type of pressure vessel, a leak type of failure is preferable to a rupture if a failure occurs.

Although the aluminum can industry strives to avoid failures altogether, some events of can failure are inevitable. Leak-Before-Break theory gives canmakers the ability to predict the response of cans whose thinwalls have been fractured. The leak versus rupture response of the can is governed by the fracture resistance, which is a property of the material, the failure hoop stress (controlled by the internal pressure and the wall thickness), and the length of the flaw that causes the fracture. In addition to fracture resistance, the puncture resistance of a particular container is important in determining whether particular containers or container designs are more or less susceptible to a failure by puncture than other containers.

Instrumented impact testing techniques have previously been used to measure puncture resistance in various containers, including pressurized aluminum containers. Instrumented impact testing is similar to conventional impact testing with the exception that in an instrumented test the force applied to the specimen, in this case the aluminum can, is measured continuously throughout the test. Two basic types of instrumented impact testing technology are known in the prior art, pendulum or drop-weight testing that use gravity to impact the specimen and servo-hydraulic or pneumatic machines that force an impactor through the specimen. The design of many of these prior art systems, which impact the side of the can from above, causes the measurements to be taken in an area of the can backed by a gas bubble, rather than a liquid. Impact in the area of a gas bubble produces results atypical of the most common conditions of external impact for end-uses of the can.

The present invention is related to an improved method and apparatus for measuring puncture resistance in aluminum cans. The puncture resistance gauge of the present invention is an improved impact-testing device that more accurately simulates typical end-use conditions of a filled aluminum can undergoing a dynamic impact with an external object. The improved puncture gauge and method of use according to the invention measures various puncture characteristics or parameters of an aluminum can during an impact event, including the force that the aluminum can is capable of absorbing before puncturing, and the deflection that the can withstands in absorbing this applied force.

SUMMARY OF THE INVENTION

The present invention provides an improved method and apparatus for measuring puncture resistance in thin aluminum beverage cans. A preferred embodiment of the disclosed puncture gauge uses a horizontal gauge configuration such that the filled sample can is upright during testing. As described below, the use of an upright sample can where the area of impact is backed by liquid more accurately simulates typical end-use conditions. A preferred embodiment of the horizontal puncture gauge also includes a carriage to removably hold the penetrator in place as it is driven down the length of the puncture gauge, preferably along a set of tracks for stability and to provide a straight path, toward the sample can.

Another feature of a preferred embodiment of the puncture gauge of the present invention is a splash chamber for containing the sample can during testing. The use of a splash chamber protects sensitive electronic measuring equipment from the spray of liquid if the impact results in a through-wall puncture. A final feature of a preferred embodiment of the invention includes a data acquisition system to collect, convert, analyze, and report test data measured from various sensors during testing. These features, described in detail below, may be used singularly or combined to test cans of various geometries under development for puncture resistance. Aluminum cans with varying sidewall thicknesses may be tested during development in an effort to achieve even thinner aluminum cans that still meet minimum threshold requirements for resisting puncture failure. Additionally, these features may be used singularly or in combination for the testing of aluminum can production batches, likewise to ensure that manufactured cans are meeting industry puncture resistance tolerances. The method of using the horizontal puncture gauge of the invention is also described below.

BRIEF DESCRIPTION OF THE DRAWINGS

The accompanying drawings are incorporated into and form a part of the specification to assist in explaining the present invention. The drawings are intended for illustrative purposes only and are not intended as exact representations of the embodiments of the present invention. The drawings further illustrate preferred examples of how the invention can be made and used and are not to be construed as limiting the inventions to only those examples illustrated and described. The various advantages and features of the present invention will be apparent from a consideration of the drawings in which.

DETAILED DESCRIPTION OF THE INVENTION

Figure 1:
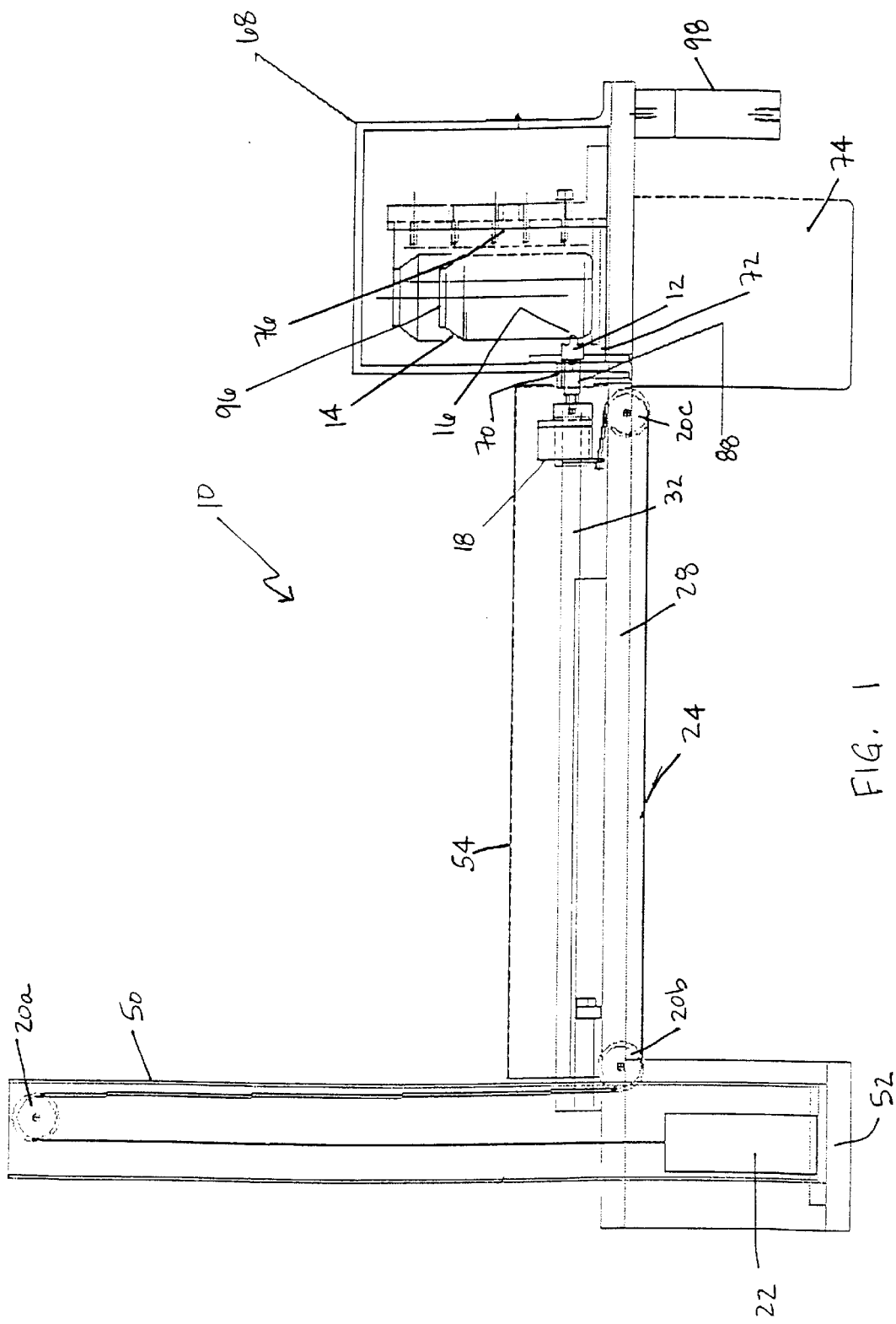
FIG. 1 shows an elevational view of a puncture gauge according to an embodiment of the present invention.

The present invention is described in the following text by reference to drawings of examples of how the invention can be made and used. The drawings are for illustrative purposes only and are not exact scale representations of the embodiments of the present invention. In these drawings, the same reference characters are used throughout the views to indicate like or corresponding parts. The embodiments shown and described herein are exemplary. Some details of the puncture gauge and its method of use are well known in the art, and as such are neither shown nor described. It is not claimed that all of the details, parts, elements, or steps described and shown were invented herein. Even though numerous characteristics and advantages of the present invention have been described in the drawings and accompanying text, the description is illustrative only, and changes may be made, especially in matters of arrangement, shape and size of the parts, within the principles of the invention to the full extent indicated by the broad general meaning of the terms used in the claims.

Analysis of puncture characteristics of pressure vessels, particularly carbonated beverage aluminum cans, using impact testing techniques provides important data that can be used in testing new can designs and materials. Puncture resistance measurements may be used during the development of new aluminum can embodiments to ensure that new designs or dimensions meet threshold functionality requirements. Such information aids engineers in designing aluminum cans that minimize metal use while maintaining the required level of structural integrity for normal end-use conditions, including anticipated dynamic impacts during processing and shipping and consumer use. Another use of puncture testing is periodic testing of production batches to determine if aluminum cans being produced meet the puncture specifications for that particular can design. Information from production batch analysis is useful in determining whether the can forming process is performing according to specification.

One of the goals of measuring a container's puncture resistance is to enable aluminum can designers to understand which design parameters influence puncture performance and how the puncture resistance is affected. Such an understanding allows can designers to intelligently develop new can designs, while taking into consideration the factors influencing performance, and compare the puncture performance of various designs. Therefore, in measuring puncture resistance or the puncture characteristics of an aluminum can, repeatability is an important aspect of the testing device. A primary purpose in puncture testing is to compare puncture data among various containers and container designs. As one of the goals of measuring a container's puncture resistance is enabling aluminum can designers to determine what design parameters influence puncture performance, it is important to be able to make comparisons between various can designs. To have a meaningful comparison between various can designs, repeatability and the minimization of the standard deviation is important. Therefore, the test penetrator or impactor of a puncture gauge used to measure puncture performance needs to be able to strike the sample container in the same location, at the same velocity, and with the same trajectory for each container tested.

In addition to repeatability, it is important that the impact-testing device, or puncture gauge, simulate actual end-use impact conditions, to the extent possible. Prior art impact-testing devices for aluminum cans typically involve dropping a weight vertically to impact the side of the can. The side of the can in the area of the thinwall is typically the area that is tested for puncture resistance as it is the area most susceptible to damage, primarily due to the fact that it is the thinnest-gauge metal in the can. In order for the vertically dropped weight of prior art testing devices to impact the side of the aluminum can, the aluminum can must be held in a horizontal position, in other words the can must be resting on its side. When on one side, a gas bubble forms along the opposite, upper side of the can, in the area in which the drop weight will impact. Impacting the can in the area of the gas bubble frequently results in an inaccurate assessment of the container's puncture performance.

Under the most typical end-use conditions, an aluminum beverage can is more likely to experience an external impact in an area filled with liquid, rather than the area of the gas bubble. Therefore, prior art impacting-testing in the area of the gas bubble produces inaccurate puncture performance data. In accordance with the present invention, it is recognized that a horizontal puncture gauge may be used for impact testing of a vertical, or upright, aluminum can. Therefore, a horizontal puncture gauge, with repeatable functionality and that provides more accurate puncture performance data, and its method of use are described according to the present invention.

Figure 2:
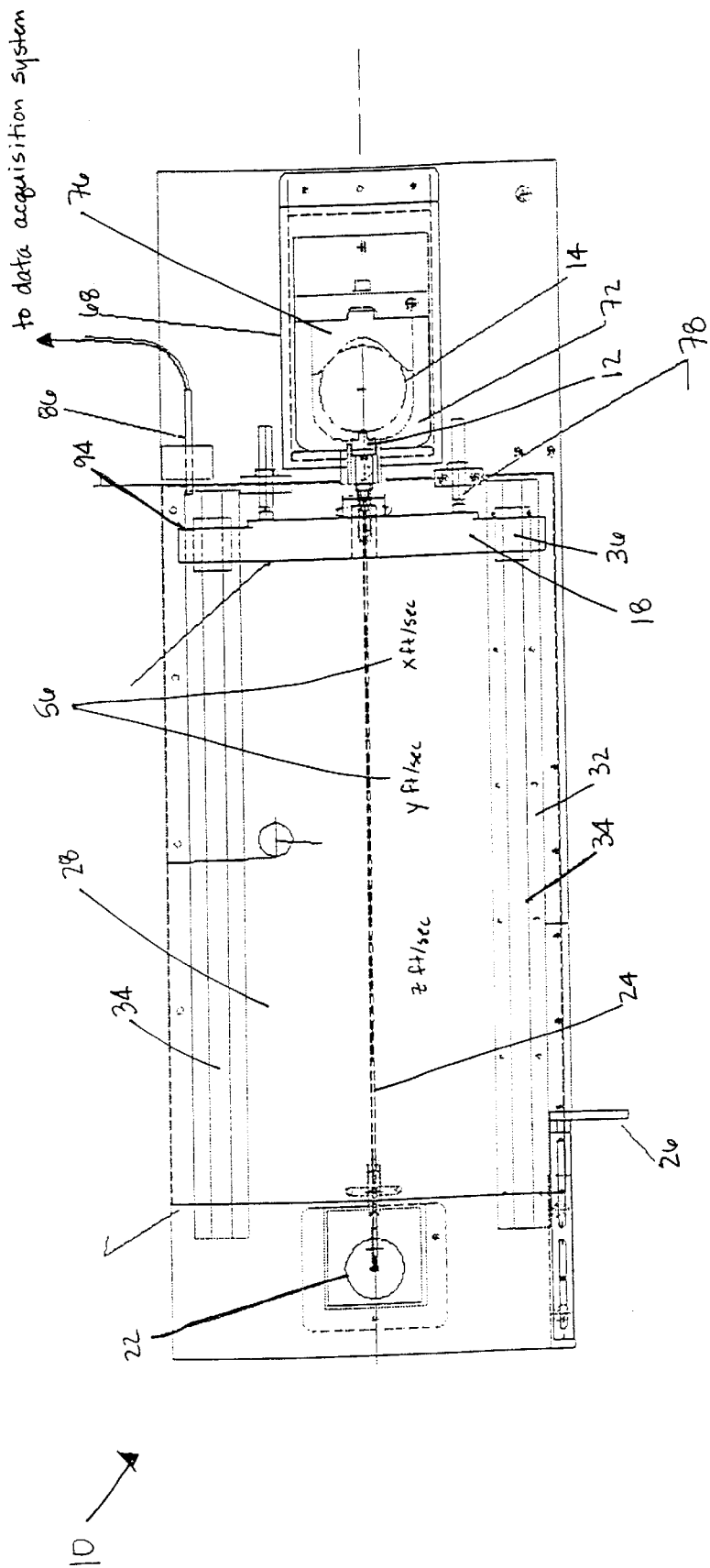
FIG. 2 shows a plan view of a puncture gauge according to an embodiment of the present invention.
Figure 4:
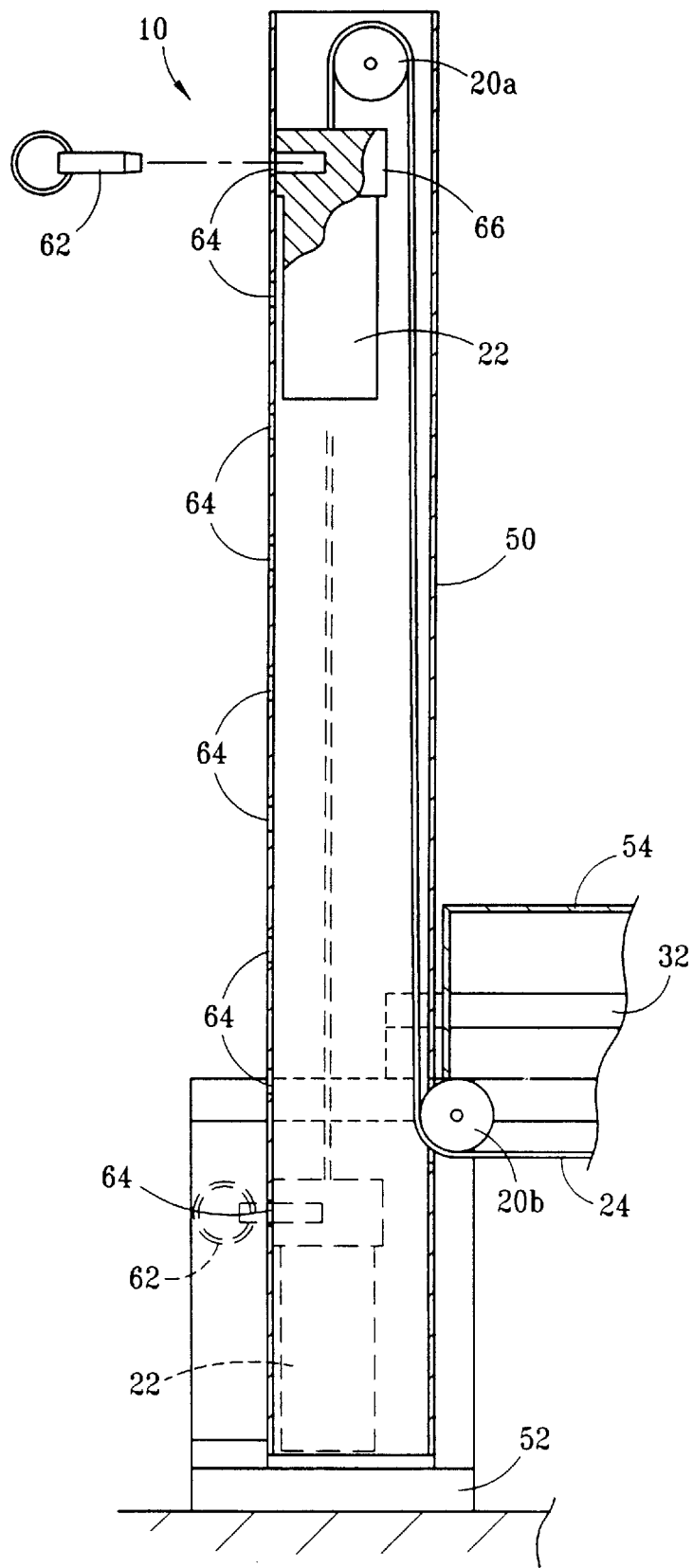
FIG. 4 shows an elevational view of a weight tower of a puncture gauge according to an alternate embodiment of the present invention.
Figure 5:
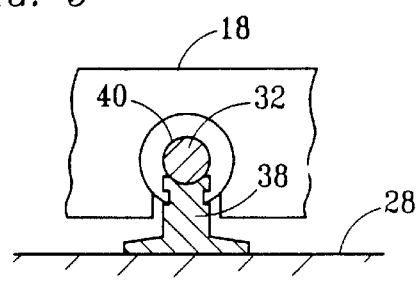
FIG. 5 shows a partial elevational view of a track and carriage of a puncture gauge according to an alternate embodiment of the present invention.
Figure 6:
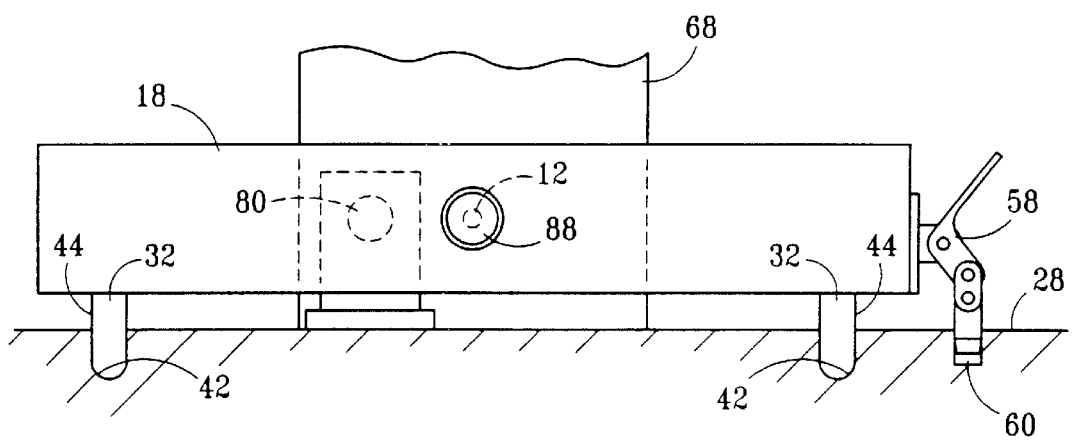
FIG. 6 shows an elevational view of a track and carriage of a puncture gauge according to an additional alternate embodiment of the present invention.
Figure 1:
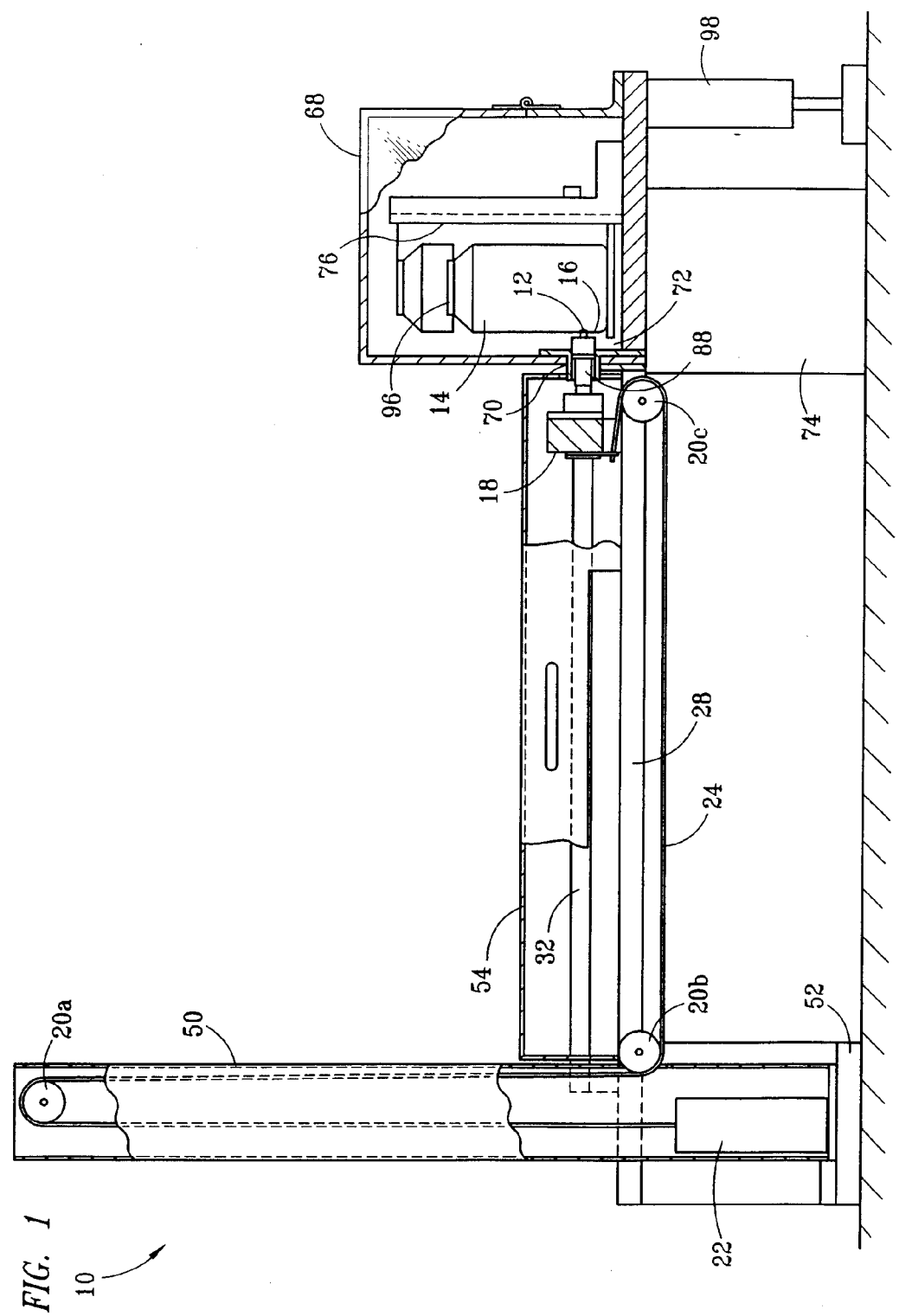
Figure 2:
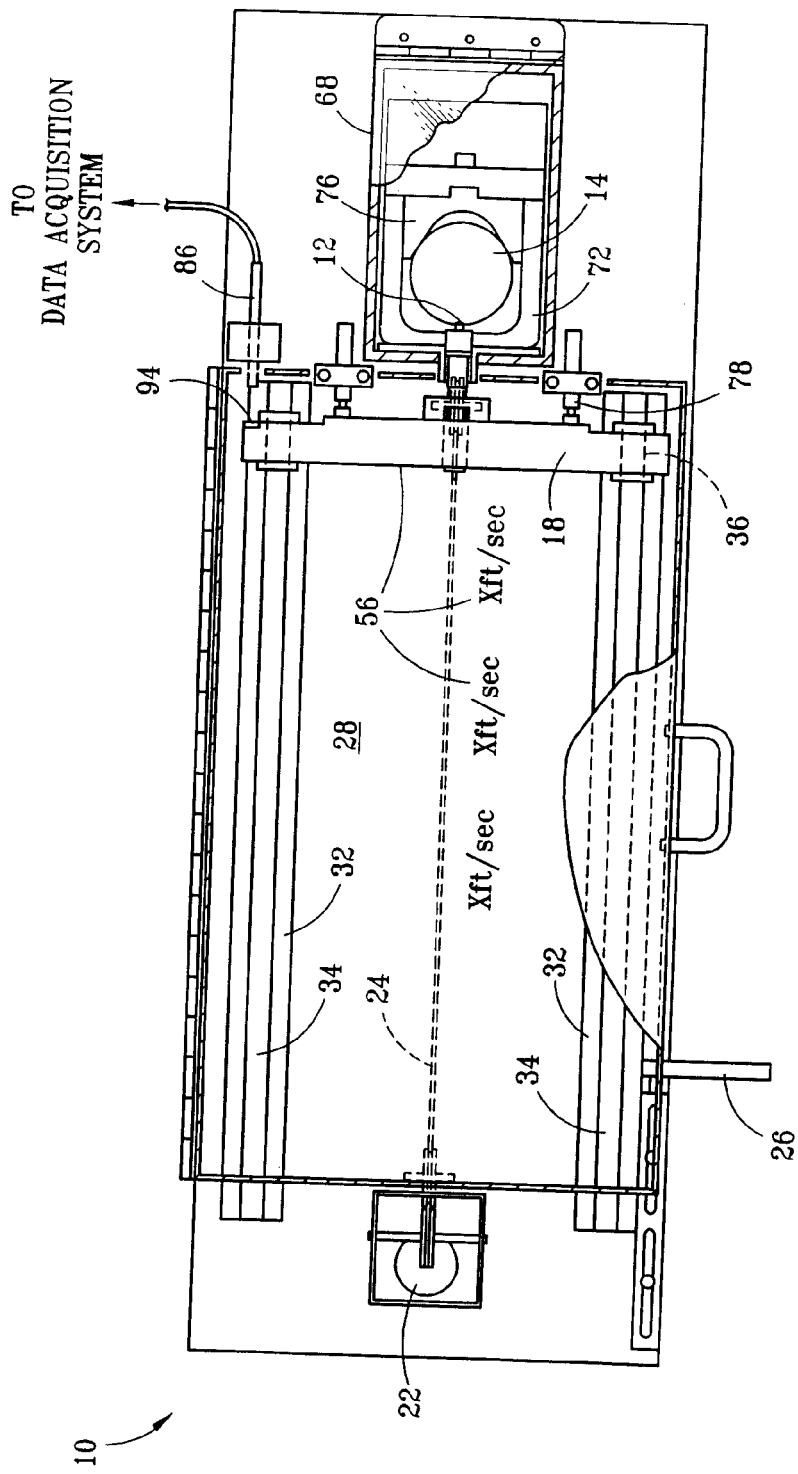

The following describes a preferred embodiment of a horizontal puncture gauge according to the present invention by reference to FIGS. 1 and 2 and to alternate embodiments by reference to FIGS. 4, 5 and 6. Although the referred and alternative embodiments are described, the description is not intended to limit the scope of the invention as defined by the claims. Additionally, although a horizontal gauge is described as specifically as a puncture gauge for use in driving a penetrator to puncture a sample aluminum can, the gauge of the invention is not limited to puncture events. The gauge may be used, by modifying force with which the penetrator impacts a sample can, to test non-puncturing impacts. Depending on the force of impact, the penetrator may or may not create a fracture in the sample can. Such non-puncturing tests are also useful in testing various can designs and production batches, as well as for identifying puncture resistance performance factors. The description of the horizontal gauge as a puncture gauge and the description of the puncture or impact event are not intended to limit the invention to testing with an actual puncture.

FIG. 1 is an elevational view of a horizontal puncture gauge 10, according to the present invention and more particularly, illustrative of a preferred embodiment of the present invention. FIG. 2 is a plan view of the same preferred embodiment of puncture gauge 10 shown in FIG. 1. The horizontal puncture gauge 10 of the present invention allows a penetrator (or impactor) 12 to impact a sample aluminum can 14 while in an upright or vertical position. Prior to testing, sample aluminum can 14 is preferably filled with liquid, pressurized, and sealed by known mechanisms not depicted in FIG. 1. Sample aluminum can 14 is typically filled with water for ease of testing and clean-up and to avoid the unmeasurable, experimentally confounding inconsistencies that can influence test results when off-the-shelf products are used, although a carbonated beverage may be used according to the invention. Although puncture gauge 10 may be modified to accommodate other sample can sizes, the preferred diameter size for sample can 14 is approximately 2.6 inches and the preferred height is approximately 4.8 inches.

The vertical position of liquid-filled sample can 14 allows penetrator 12 to impact a thinwall region 16 of sample can 14 under circumstances in which the thinwall region 16 is filled with liquid. Impact of the thinwall region 16 when it is backed by liquid, as opposed to a gas bubble, more accurately simulates most typical end-use conditions, in which an aluminum beverage can is more likely to experience an external impact in an area filled with liquid than in a gas bubble area. Puncture gauge 10 can also be modified so that penetrator 12 impacts the sidewall of sample can 14 at locations above or below the thinwall region 16, while still impacting in an area backed by liquid. In the upright position, the gas bubble is located only in the upper-most portion (near the lid) of sample can 14. If it is desired to test the sidewall of sample can 14 near the lid without the gas bubble, sample can 14 can easily be placed in an upside down position such that the gas bubble would move from the top (now at the lowest position) to the bottom (now at the highest position) of sample can 14.

In a preferred embodiment of puncture gauge 10, penetrator 12 is housed in a carriage 18 such that both carriage 18 and penetrator 12 move toward sample can 14, although it is not necessary to have a carriage as depicted and described as long as penetrator 12 is capable of being driven by some driving force toward sample can 14. Carriage 18 is preferably physically connected to puncture gauge 10, as described below. Carriage 18 also preferably slides or rolls along the length of puncture gauge 10 by bearings (not shown), maintaining physical contact with puncture gauge 10, toward sample can 14. The movement of carriage 18 along the length of puncture gauge 10 is discussed further below. The use of carriage 18 allows penetrator 12 to impact sample aluminum can 14 at the same location and same angle for each test. The preferred location for impact of penetrator 12 is the thinwall region 16 of sample can 14, although other locations may be tested by varying the vertical position of carriage 18 or the vertical position of penetrator 12 in carriage 18 relative to sample can 14. The preferred angle of impact is 90°, although other angles may be tested by varying the angle of penetrator 12 in carriage 18.

Preferably, penetrator 12 projects from the edge of carriage 18 so that only penetrator 12, and not carriage 18, impacts sample can 14. Penetrator 12 is most preferably cylindrical with a hemispherical head or tip for impacting sample can 14, although other penetrator shapes may be used according to the invention. Other end shapes for penetrator 12 may include a pointed end, a blunt end, or an irregularly shaped end. Additionally, the tip of penetrator 12 may be of varying sizes. The most preferable penetrator 12 is a hemispherical tipped penetrator with a diameter between 0.125 and 0.375 inches. Penetrator size greatly affects the results of the impact event. Other penetrator tip sizes, most typically up to about 0.5 inches, may also be used with puncture gauge 10. However, penetrator sizes approaching 0.5 inches in diameter tend to result in an impact with sample can 14 that is more like crushing that puncturing. Penetrator 12 is most preferably detachably connected to carriage 18, and more specifically to a sensor attached to carriage 18 as described below, to allow penetrator 12 to be easily removed and replaced. However, it is important that carriage 18, or a sensor attached to carriage 18, securely hold penetrator 12 so that the penetrator 12 does not become dislodged during impact with sample can 14.

Additionally, for repeatable comparisons between various sample cans 14, penetrator 12 should be of equal length for each test comparison conducted. Various lengths may be used for penetrators 12 if it is desired to make comparisons between different penetrator sizes, but consistent length should be used for any given test run or batch of sample cans 14. The tips of penetrators 12 should be of a known surface roughness, and the surface roughness should be monitored periodically during testing so that penetrator 12 may be replaced if necessary. Penetrator 12 most preferably has a tip manufactured at a surface roughness of RMS value of 4–8, a "mirror finish" surface, but other surface roughness values may be used according to the invention. The tip of penetrator 12 should also be manufactured out of a material that is considerably harder than the surface being impacted, the thinwall 16 of sample can 14. The tip of penetrator 12 is most preferably made of tool steel. Anodized aluminum tips have also been used by Applicants, but over time, the anodized coating wore off, and the tips became rougher, which affected the repeatability of the tests.

Like prior art vertical drop-weight testing devices, which use gravity to drive the penetrator to impact the specimen, the horizontal puncture gauge 10 of the invention may also use gravity to drive the penetrator 12. A gravity driven pulley and weight system is the most preferable driving force for the present invention due to its simplicity. Pulleys 20 are connected to a weight 22 by a tow cable 24. Pulleys 20 are also connected to penetrator 12, and more specifically to carriage 18 that holds penetrator 12, by tow cable 24. It is preferred that three pulleys 20 (labeled 20a, 20b, and 20c) be used, but fewer or more pulleys may be used depending on the configuration of weight 22 in relation to the other components of puncture gauge 10 as discussed below. When weight 22 is released, pulley 20 and tow cable 24 drive carriage 18, and therefore penetrator 12, toward sample aluminum can 14. Weight 22 is released by actuating release lever 26. Release lever 26 may be any mechanism of releasably securing weight 22 in an elevated position so that when release lever 26 is actuated, weight 22 falls by force of gravity and drives penetrator 12 toward sample can 14. Release lever 26 may be connected to tow cable 24 by a pinching or other securing mechanism to hold weight 22 in an elevated position. Alternatively, release lever 26 may be any mechanism of releasably securing carriage 18 in its initial starting position. Other variations of securing carriage 18 or weight 22 in an initial starting position for an impact test are discussed below.

The use of a pulley and a falling weight as a driving force is well known in the art. The pulley and weight system of the present invention allows relatively consistent speed for movement of carriage 18 toward sample aluminum can 14, which in turns aids in the repeatability of impact testing. In addition to a gravity driven system, other mechanical or electromechanical driving forces may be used according to the present invention to move penetrator 12 into contact with sample aluminum can 14.

Although the use of carriage 18 to hold penetrator 12 in the pulley and weight driven system is preferred, other driving systems may not require use of carriage 18. One possible embodiment for puncture gauge 10 that would not require a carriage, such as carriage 18, to move penetrator 12 toward sample can 14 is a ballistic driving system (not depicted in FIGS. 1 and 2). In such a system, penetrator 12 would be fired toward sample can 14. In a ballistic type system, penetrator 12 would not be physically connected to puncture gauge 10 after being fired, but would be tethered to a sensor, such as a load cell, for measuring the load at impact. As penetrator 12 in this embodiment would not be attached to puncture gauge 10, the forces of gravity would have an effect on the trajectory of penetrator 12. Due to the gravitational forces acting on penetrator 12 in this type of system, penetrator 12 may not impact sample can 14 at the same location or at the same angle for each test, which may affect the desired repeatability of puncture gauge 10. However, due to the relatively short distance penetrator 12 travels before impacting sample can 14, the change in trajectory, impact angle, and location may be negligible.

It is still preferred to eliminate as many variables as possible in the use of puncture gauge 10 that may effect the repeatability of its results, therefore, it is preferred to have penetrator 12 physically connected to some path along the length of puncture gauge 10 so that penetrator 12 travels the same path and impacts sample can 14 at the same location and angle for each test. The most preferable embodiment is for penetrator 12 to be held by carriage 18, which rests on or is actually attached to puncture gauge 10 as described further below. The use of carriage 18 is also preferred because it houses other components of puncture gauge 10 described below.

Puncture gauge 10 also includes a base plate, or main plate, 28 along which carriage 18, and penetrator 12, are driven toward sample aluminum can 14. Base plate 28 may be any flat surface allowing horizontal movement of carriage 18, and therefore penetrator 12, toward sample aluminum can 14. Carriage 18 travels along base plate 28 toward sample can 14, preferably in a straight line. Base plate 28 preferably has a track 32 along which carriage 18 moves. Track 32 is best seen in FIG. 2. Track 32 keeps carriage 18 moving, preferably in a straight line, on base plate 28 toward sample aluminum can 14. It is not necessary for carriage 18 to have wheels to move along track 32, as carriage 18 may slide along track 32 as weight 22 falls from its elevated position, but wheels may be added if desired and it is preferred that carriage 18 have bearings (not shown) to reduce the frictional forces as carriage 18 moves along track 32. Track 32 most preferably comprises two raised rails 34 which correspond to rail openings 36 in carriage 18. Rails 34 are raised relative to base plate 28 and are most preferably located near the outside edges of base plate 28. Rail openings 36 are located to correspond to rails 34.

Rails 34 and rail openings 36 are preferably rounded, being circular, U-shaped, or other tubular shape; however, other shapes may be used according to the invention. Track 32 may also include any other device that maintains carriage 18 on a path along base plate 28.

Track 32 may also comprise a single rail 38 (as shown in FIG. 5), which corresponds to a single rail opening 40 in carriage 18. Rail 38 is preferably located near the center of base plate 28 for improved stability of carriage 18; however, rail 38 may be located anywhere along base plate 28.

Alternatively, track 32 may comprise two grooves 42 (as shown in FIG. 6) in base plate 28, which correspond to two runners 44 protruding from carriage 18. Grooves 42 are indentations in base plate 28. Runners 44 fit in grooves 42 to keep carriage 18 moving along a path on base plate 28 as it is driven towards sample aluminum can 14. Grooves 42 are preferably located near the outside edges of base plate 28 for improved stability of carriage 18. Grooves 42 are also preferably rounded or U-shaped and runners 44 are likewise shaped to rest in and allow movement along the grooves 42. Grooves 42 and runner 44 may be any other shape allowing movement of carriage 18 along track 32. As an additional alternative, track 32 may include a single groove indented into base plate 28, which corresponds to a single runner protruding from carriage 18. A single groove is preferably located near the center of base plate 28 for improved stability of carriage 18; however, a single groove may be located anywhere along base plate 28. A single groove and single runner may be shaped as described above for grooves 42 and runners 44, and are preferably rounded or U-shaped.

Puncture gauge 10 also preferably includes a weight tower 50 to house weight 22. Tower 50 aids in improving the safety of operation of puncture gauge 10 by closing off moving parts, such as falling weight 22, pulley 20a, and tow cable 24, to reduce the risk of injury to bystanders. Tower 50 preferably has a tower base 52, which supports weight 22 when it has fallen to its lowest desired position. Tower base 52 most preferably includes a cushion or shock pad to avoid hard impact of weight 22 against tower base 52. In FIG. 1, tower 50 is located partially above the plane of base plate 28 and partially below the plane of base plate 28, such that tower base 52 is below base plate 28. In this configuration, tower 50 provides support for a pulley 20a located near the top of tower 50 and for tower base 52. Tower base 52 provides a support for weight 22 in its fallen position. Tower base 52 may be sized to be the same width as tower 50, or may be wider than 50. Tower base 52 may also be the floor of a room housing puncture gauge 10. Alternatively, tower 50 may be placed so that it is entirely above or below the plane of base plate 28.

In the embodiment where tower 50 is located entirely below the plane of base plate 28, pulley 20a may be eliminated from puncture gauge 10. In that configuration, it is easy to utilize the floor of a room housing puncture gauge 10 as tower base 52, but base plate 28 would need to be sufficiently elevated to provide enough falling room for weight 22 to be able to drive carriage 18 so that penetrator 12 makes contact with sample can 14. Additionally, the actual tower 50 may be eliminated in this configuration where the tower 50 is not needed to provide structural support to pulley 20a or to tower base 52, if the floor is utilized as tower base 52. Although it is not necessary to have tower 50 in this configuration, it is still preferred to include tower 50 as a safety mechanism to reduce risk of injury by moving parts of puncture gauge 10 during operation. If tower base 52 is not the floor (or a stool or a box or some other support mechanism not connected to puncture gauge 10), then some configuration of tower 50 would be needed to support tower base 52. Alternatively, in the embodiment where tower 52 is located entirely above the plane of base plate 28, tower base 52 may be an extension of base plate 28 or may be the table or other surface on which base plate 28 rests.

Puncture gauge 10 also preferably includes a cover 54 that fits over base plate 28. Cover 54 is sized to fit over base plate 28 with a height to accommodate carriage 18. Cover 54 is removable to allow access to the components of puncture gauge 10, particularly the base plate 28, carriage 18, penetrator 12, tow cable 24, and sensor components discussed below. Cover 54 may simply be placed over base plate 28 or may be hinged to base plate 28. Additionally, cover 54 may be sized to fit over the entire puncture gauge 10. Cover 54 aids in the safety of operation of puncture gauge 10 during operation by closing off the moving parts of the gauge to reduce risk of injury to bystanders.

Base plate 28 may also include velocity markings 56. Velocity markings 56 are best seen in FIG. 2. The velocity markings 56 comprise numbers indicating the approximate velocity for movement of carriage 18 base plate 28 at various distances from sample can 14. Velocity markings 56 are not required for puncture gauge 10, as the velocity of the impact is preferably actually measured as discussed below, but they are preferred to aid in determining a starting point for release of carriage 18 during a testing event. Velocity markings 56 may be in any units of distance per time desired, such as feet/second or meters/second. The puncture gauge 10 of the present invention preferably measures puncture resistance at velocities up to 14 (fourteen) feet/second, but higher velocities may be achieved by the appropriate combination of components. The value for velocity markings 56 increases with distance away from sample can 14.

Values for velocity markings 56 may be determined according to the driving force applied to move carriage 18. In the preferred gravity driven pulley and weight system, the various velocities indicated by markings 56 are easily calculated according to known equations based on the value (or weight) of weight 22, the weight of carriage 18, and the distance from sample can 14. Values for velocity markings 56 are preferably determined experimentally, by a series of calibration tests, which include marking the starting point for release of carriage 18 and later noting the velocity recorded for that test. For non-gravity driving systems, the values for velocity markings 56 can be determined in the same manner.

Calculation of the velocity is preferably automatically determined by sensor equipment or may be manually measured according to the particular distance from sample can 14 and the time it takes penetrator 12 to impact sample can 14. For impacting testing with puncture gauge 10, velocity at impact is the velocity of concern and is measured. The velocity of carriage 18 increases as carriage 18 is being accelerated by falling weight 22 up to the "terminal velocity" where weight 22 hits tower base 52.

In addition to releasably securing carriage 18 via release lever 26, carriage 18 may include an anchor 58 (as shown in FIG. 6) that secures carriage 18 at a fixed position on base plate 28. Anchor 58 can be any clip, pin, or clamping device that may be used to secure carriage 18 at a particular starting point along base plate 28. Additionally, anchor 58 may correspond to anchor-holes 60 (as shown in FIG. 6) on base plate 28. Alternatively, anchor-holes 60 may be located on track 32. It is preferred that a completely removable anchor 58 be used with carriage 18. As an additional alternative, release lever 26 may actuate movement of anchor 58 to secure or release carriage 18 from an initial starting point.

When anchor 58, or release lever 26, is raised or removed, carriage 18 can be positioned anywhere along base plate 28 as a starting point for the distance over which carriage 18 will travel to impact sample can 14. Once carriage 18 is located at the desired starting point, anchor 58 may be used to secure carriage 18 in place until the other components of puncture gauge 10 are ready to being the impact test. Velocity markings 56 may be used to identify a starting point for release of carriage 18 for an approximate desired velocity or velocity range. Carriage 18 may be released at the beginning of the test by raising or removing anchor 58. Alternatively, anchor 58 may be used to hold carriage 18 at a location beyond the intended starting point and, when ready, anchor 58 can be raised or removed and carriage 18 can be manually positioned at the desired starting point and then released.

An additional alternative to release lever 26, is that tower 50 may include a weight position pin 62 (as shown in FIG. 4) to secure weight 22 at any vertical position in tower 50. Pin 62 is shaped to fit into pin-holes 64 along the length of tower 50 and to fit into a pin ring 66 located somewhere on weight 22. Weight 22 may be positioned in the desired starting position, which in turn sets the position of carriage 18 as carriage 18 is connected to weight 22 by tow cable 24, and pin 62 may be insert through a pin-hole 64 and pin ring 66 to secure weight 22 and carriage 18 in place. Pin 62 may be any clip or clamp capable of securing weight 22 in position.

Sample aluminum can 14 is preferably housed at the end of base plate 28 in a splash chamber 68. Splash chamber 68 helps contain the liquid contents of sample can 14 once pierced by impact with penetrator 12. Without splash chamber 68, the contents of sample can 14 would be sprayed all over the puncture gauge 10 and the surrounding testing facility when sample can 14 is pierced by penetrator 12 thereby releasing the pressure of sample can 14. Splash chamber 68 is preferably constructed of transparent material, such as plexi-glass, so that the results of the impact between penetrator 12 and sample can 14 can be viewed. The shape and size of splash chamber 68 must be such that it can accommodate the shape and size of sample can 14. Splash chamber 68 is also preferably detachably connected to puncture gauge 10, and most preferably to base plate 28. The connection allows splash chamber 68 to be removed for cleaning and repair, while also securely holding splash chamber 68 in place during impact. Splash chamber 68 preferably has a removable top so that the walls of the splash chamber need not be removed to insert or remove sample cans 14 or to clean the interior of splash chamber 68.

Splash chamber 68 should be as enclosed as possible in order to contain the majority of the contents of sample can 14 upon puncture. Preferably, splash chamber 68 encloses sample can 14 on at least 5 sides (front, top, back, and two sides) for a rectangular or cubic shaped chamber, with the front side (impact side) of splash chamber 68 having a penetrator opening 70 large enough to allow penetrator 12 to pass through to impact sample can 14. The bottom of the chamber area may be base plate 28 or may be an additional side of splash chamber 68. It is preferred that the bottom of the chamber area be base plate 28 and that base plate 28 contain a drain, or other opening, 72 to allow the contents of sample can 14 to be discharged from the area of splash chamber 68 after puncture. Alternatively, if splash chamber 68 has a bottom side, then both the bottom side and base plate 28 would have corresponding drain openings 72. In the preferred embodiment there is a catch basin 74 located under drain 72 to collect the discharged contents of sample can 14. Catch basin is preferable removably attached to base plate 28. Alternatively, a laboratory or other testing facility sink may be used as catch basin 74, without requiring catch basin 74 to be attached to puncture gauge 10. In this configuration, puncture gauge 10 is positioned over a sink-type catch basin 74 so that drain opening 72 is aligned with the sink-type catch basin 74.

Splash chamber 68 also preferably includes sample can support 76. Sample can 14 snugly rests against support 76 to stabilize sample can 14 during impact. Support 76 preferably maintains sample can 14 in an up-right position in splash chamber 68 throughout testing. Support 76 may be used even if splash chamber 68 is not used. Support 76 is preferably a V-shaped support, referred to as a V-block, that is approximately as long as sample can 14.

Puncture gauge 10 also includes shock absorbers 78 that stop carriage 18 from impacting splash chamber 68, or sample can 14, during testing. Shock absorbers 78 are best seen in FIG. 2. Shock absorbers 78 are preferably located alongside and slightly in front of splash chamber 68 and inside track 32 such that they contact carriage 18 without impeding penetrator 12 from passing through penetrator opening 70, although other configurations that do not interfere with penetrator 12 contacting sample can 14 may be used in accordance with the invention. Shock absorbers 78 are most preferably attached to base plate 28 using any mechanical fastening method. Shock absorbers 78 may also be attached to splash chamber 68 or track 32. Additionally, a single shock absorber 80 (as shown in FIG. 6) may also be used. Single shock absorber 80 is preferably located near the center of base plate 28, but may be located anywhere along the width of base plate 28 and slightly in front of splash chamber 68, or sample can 14, that does not interfere with penetrator 12 contacting sample can 14.

Puncture gauge 10 also includes a data acquisition system for compiling and analyzing testing data. The data acquisition system is preferably capable of both automatic measurement of testing data through sensors and manual data input. Any hardware used in the data acquisition system associated with sensor-compiled data should have a very quick response frequency because the impact of penetrator 12 and sample can 14, when the measurements are made, lasts approximately 0.002–0.006 seconds. The data acquisition system preferably includes a computer or other recording and data compilation device, a displacement transducer 86 (as shown in FIG. 2), and a load cell 88 (as shown in FIG. 1) for sensing and recording various parameters during testing, and a data acquisition card, or data acquisition board. The data acquisition system is most preferably operated according to the steps outlined in FIG. 3 and described below.

The computer can be any device capable of receiving, storing in memory, analyzing, and printing (if connecting to a printing device) test data directly from sensors on puncture gauge 10 and from manual input. The computer most preferably includes a monitor and includes specific puncture gauge data acquisition programming and is connected to a data acquisition card capable of acquiring, formatting and analyzing test data according to various equations or logic statements, prompting testing personnel for input of required data, and generating graphical representations of test results. While these capabilities are preferred, puncture gauge 10 may be used according to the invention with only some of these functions.

The data acquisition card is most preferably a National Instruments model number PCI-6110E card. Other data acquisition cards may be used according to the invention as long as they are compatible with the other components of the data acquisition system. The data acquisition card may be connected to the computer as a plug-in board to transfer test data directly to a memory in the computer. Alternatively, the data acquisition card may be remote from and connected to the computer via a parallel or serial port. The puncture gauge data acquisition programming is most preferably created in the programming environment Labview from National Instruments, but other programming environments may be used to achieve the desired functionality. The functionalities of programming in Labview are well known in the art.

Displacement transducer 86 is an optical device that emits a low powered laser beam, which is reflected off a target mirror 94 and returns to displacement transducer slightly out of phase. Displacement transducer 86 is most preferably a Philtec model number D169 optical displacement transducer with a range of 0–0.875 inches and a sensitivity of ±0.0015 inches. Other displacement transducers may be used according to the invention as long as they are compatible with the other components of the data acquisition system. Displacement transducer 86 is preferably located near sample can 14, outside of splash chamber 68 so that it is protected from the spray at impact. Target mirror 94 is preferably located on carriage 18 and is aligned with displacement transducer 86. The phase shift in the laser beam from displacement transducer 86 can be used to calculate displacement at impact. Displacement transducer 86 can be sample up to 400,000 times per second for accurate displacement measurements with a resolution of 0.001 inch. The displacement measurement can be coupled with the measurement of elapsed time to give an accurate velocity measurement for the test. In addition to safety reasons, cover 54 is also preferably used to reduce the sensitivity of displacement transducer 86 to changes in the ambient light of the testing facility.

Load cell 88 is used to measure the load at impact. Load cell 88 is most preferably a PCB Piezotronics model number 208M135 penetration style load cell with a range of 0–100 pounds and a sensitivity of ±0.002 pounds. Other load cells may be used according to the invention as long as they are compatible with the other components of the data acquisition system. Load cell 88 is preferably located on carriage 18 behind penetrator 12. Penetrator 12 is preferably designed to attachably interface with load cell 88, by matching thread size and pitch and proper correspondence between male and female threads. The operation and components of a displacement transducer and a piezoelectric load cell, such as transducer 86 and load cell 88, are well known in the art and further description of their operation is not required. Both transducer 86 and load cell 88 are connected to send data to a computer, and more particularly are connected to a data acquisition card, which is connected to a computer. These types of connections and their configurations are well known in the art.

Figure 3:
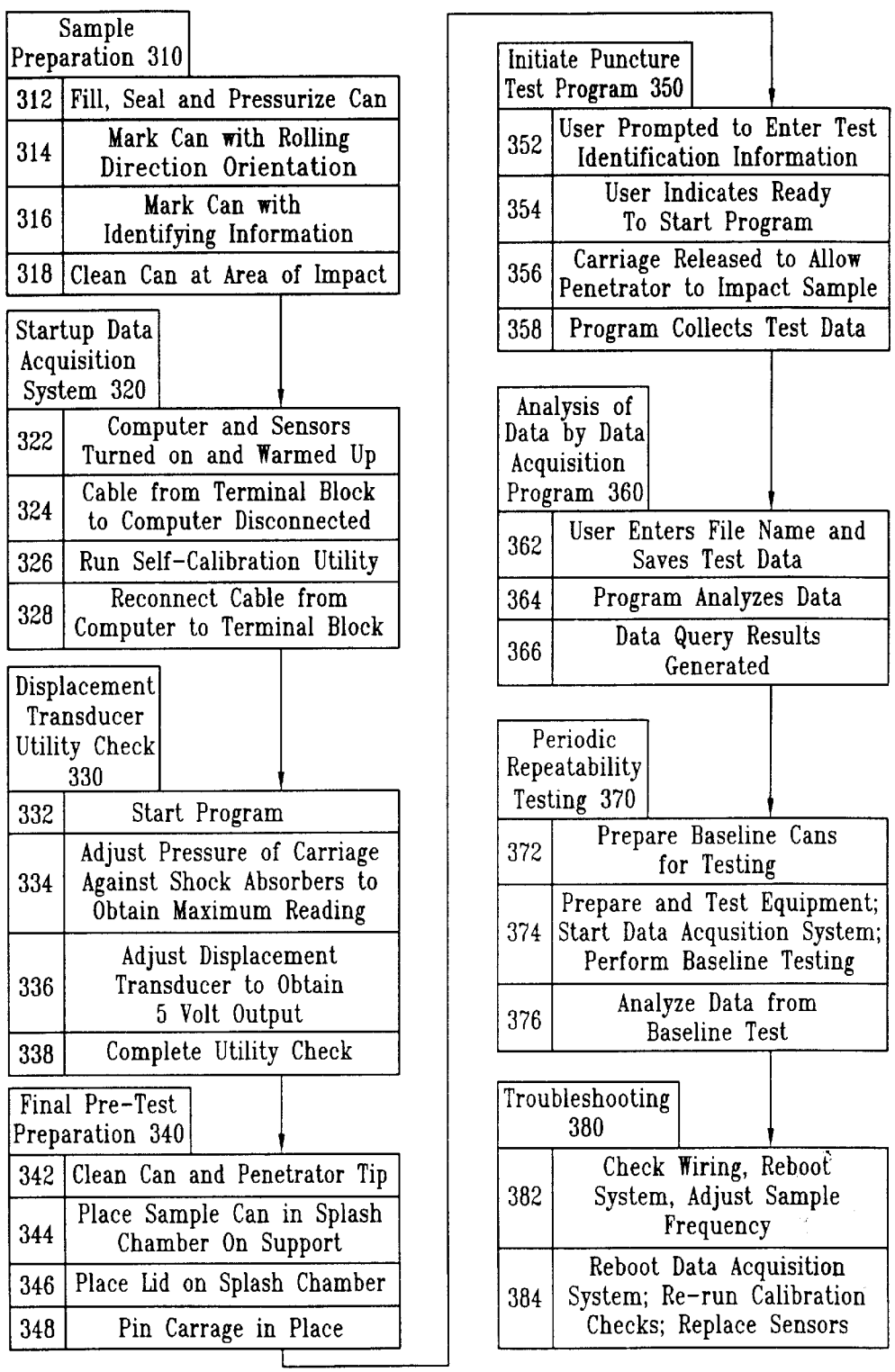
FIG. 3 shows a flow chart for the method of testing puncture resistance according to the present invention.

A computer and appropriate programming may be used to compile, format, and save testing data from puncture gauge 10, according to the steps outlined in FIG. 3. Data values such as load, displacement, and elapsed time are recorded at a given sample frequency. Other data values, such as internal pressure in sample can 14 may be measured according to known technologies. The programming preferably also allows for manual input of data, such as notes regarding the particular test and a file name for the test.

In addition to testing the puncture performance of a can's sidewall with puncture gauge 10, an end 96 (which refers to either a lid end or a domed bottom) of sample can 14 may be tested according to the invention with puncture gauge 10. Modifications to the configuration of puncture gauge 10 as described and depicted in FIGS. 1, 2, 4 5 and 6 may easily be made to accommodate testing the end 96 of sample can 14. Sample can 14 may be placed on its side in splash chamber 68 so that an end 96 of sample can 14 is facing the penetrator 12. The vertical level of the penetrator 12 in carriage 18 may need to be modified for penetrator 12 to contact end 96. With sample can 14 on its side, the majority of end 96 would be backed with liquid, as is preferred for testing thinwall region 16. As with testing thinwall region 16, it is preferred that end 96 be backed by liquid to more accurately simulate end-use conditions of dynamic external impact. The ends 96 of an aluminum can are typically considered more puncture resistant than the thinwall region 16; therefore, the puncture performance of an end 96 may not frequently be tested. However, ends 96 may be tested according to the present invention and useful data regarding puncture performance may be obtained.

In the preferred embodiment of FIG. 1, puncture gauge 10 has at least one supporting leg 98. Supporting leg 98 may support puncture gauge 10 on the surface of a table or other surface where puncture gauge 10 is set to operate. Supporting leg 98 may be used alone, or in combination with other legs 98 or in combination with tower base 52 or catch basin 74. If used alone, supporting leg 98 is preferably located near the middle of base plate 28. It is preferred to use supporting leg 98 in combination with at least one other supporting leg, where supporting legs 98 are located near the ends of base plate 28. Supporting leg or legs 98 preferably include leveling feet so that puncture gauge 10 may be leveled. Alternatively, supporting leg or legs 98 may be used in combination with tower base 52 or catch basin 74 for positioning and supporting puncture gauge 10 on a testing surface. The puncture gauge 10 depicted in FIG. 1 is not drawn to scale; therefore, tower base 52, catch basin 74, and supporting leg 98 do not appear to be on the same base plane (such as a surface of a testing table).

The following is a description of the preferred method for using a horizontal puncture gauge as described herein by reference to FIG. 3. FIG. 3 is a flow chart describing the preferred method of operating a horizontal puncture gauge according to the present invention. Although the preferred method is described, the description is not intended to limit the scope of the invention as defined by the claims. Additionally, although the method is described in terms of a puncture event, the invention is not limited to puncture events and may be used for testing non-puncturing impacts. It is preferred that the steps be carried out in the order described; however, the order of many of the steps is not critical and variations in the order may be made in accordance with the invention. Additionally, it is also not critical that each step described below be carried out to operate a horizontal puncture gauge in accordance with the invention.

The first step 310 in a preferred method of testing the puncture resistance of an aluminum can according to the present invention is to prepare the sample aluminum can for testing. In step 312, the sample can is filled, sealed, and pressurized. The sample can is preferably filled with water, although carbonated beverage may be used. The sample can is preferably pressurized through a septum with a needle attached to a tank of gaseous nitrogen regulated at the desired can internal pressure, but other pressurization methods may be used. It is preferred that the sample can be filled with approximately 355 mL of liquid, the standard amount for 12 ounce beverage containers, although other amounts may be used. It is important according to the present invention that the penetrator impact the sample can in an area, preferably the thinwall area, that is backed by liquid, as opposed to a gas bubble, to more accurately simulate external-impact under typical end-use conditions. Therefore, the sample can should be filled with enough liquid so that the liquid level when the sample can is placed in the puncture gauge is above the level where the penetrator will impact the can. The sample can is then sealed and pressurized. The sample can may be pressurized to any appropriate level for testing, and preferably is pressurized to the range of pressures which at which canned beverages are typically pressured, that being 10–90 psi. Methods for filling, sealing, and pressurizing aluminum cans are well known in the art and are not discussed in detail herein.

At step 314 the rolling direction orientation of the sample can is also marked. It is preferred that the can be marked in the thickwall area, but other areas may be marked provided that the area marked will not be in contact with the penetrator. The sample can is marked with a name or sample number or both at step 316. The final sample preparation step is to clean the sample can in the area of impact at step 318. The sample can is preferably cleaned with a gauze pad dampened with methanol. Similarly, cleaning of the puncture tip is also preferred. Other types of cleaners may also be used. This removes all contaminants, such as dirt and oil, which may effect the results of the puncture test.

The next step in a preferred method of operating the horizontal puncture gauge according to the invention is 320, start-up of the data acquisition system. As described above, the data acquisition system preferably comprises a computer, software or programming, and various sensors, such as a displacement transducer and a load cell, to detect testing data. At step 322, a computer and all sensors, including a displacement transducer and a load cell, are turned on and allowed to "warm up" for approximately 15 minutes. A cable that connects a terminal block for data acquisition to the computer is disconnected at 324. The system, and particularly a data acquisition card or data acquisition board, is preferably calibrated, or zeroed, before each testing session at by running a self-calibration utility at 326. It is not necessary that the system be calibrated before each sample in a test session. A self-calibration utility zeroes a data acquisition board against offsets in temperature and other extraneous variables. This type of programming is well known in the art and is not described in detail herein. At step 326, the cable that connects the terminal block to the computer is reconnected.

A displacement transducer check utility is preferably run at step 330. Displacement transducer check utility programming is started at step 332. This programming checks the gain setting of a displacement transducer. The displacement transducer is sensitive to changes in the reflectivity of a target mirror, ambient light, and alignment of the transducer head. Resetting the gain before each testing session is preferred to reduce long-term experimental error from the displacement transducer; however, it is not required that the gain be reset before each testing session according to the invention. It is not necessary to run this check before each sample. The programming necessary to conduct this check of the displacement transducer will be understood by those skilled in the art based on the description of the steps below and the details of the programming are not described in detail herein. Once the displacement transducer utility check programming is started, a carriage holding a penetrator is pushed against shock absorbers and the pressure of the carriage against the shock absorbers is adjusted until a maximum reading is obtained at step 334. The reading is preferably displayed on a monitor connected to the computer. Only small amounts of pressure are required in pushing the carriage against the shock absorbers.

The displacement transducer includes a small screw or other mechanism for adjusting the fine gain. This screw is adjusted until the transducer has a maximum voltage reading of approximately 5 volts at step 336. The displacement transducer check utility is completed at step 338, once the fine gain on the transducer is adjusted. Caution should be used to avoid touching or adjusting the target mirror. If the mirror is inadvertently touched or adjusted, it is preferred that the gain calibration of step 330 be repeated to avoid erroneous displacement data.

Final pre-test preparation is carried out at step 340. Step 340 preferably includes cleaning the sample can with methanol in the area of impact, if not already done, and cleaning the penetrator tip with methanol at step 342. Other types of cleaners may also be used. Cleaning the impact area of the sample can and the tip of the penetrator prior to testing removes contaminants, such as dirt and oil, which may affect test results. At this point, or at any time prior to cleaning the tip of the penetrator, the penetrator may be replaced or changed. Penetrators of varying sizes or tip shapes and various materials and surface roughness values may be used according to the invention, as previously described. The surface roughness of the penetrator should be inspected and measured periodically during testing to ensure that the surface has not become too rough compared to the starting roughness. Each impact with a sample can may roughen the surface of the penetrator. The penetrator is preferably periodically replaced.

The sample can is preferably placed in a splash chamber resting upon a support at step 344. A splash chamber is preferably used to protect sensitive electronic components, such as the displacement transducer and load cell of the horizontal puncture gauge from the spray of liquid from the sample can at impact. A support, and preferably a V-block, is placed behind the sample can to keep the sample can in position during the impact event. The sample can is preferably placed in the splash chamber so that the cleaned impact area faces the penetrator. A lid is preferably placed on the splash chamber at step 346. At step 348, the carriage is preferably moved beyond (farther from the sample can than) the desired start or release point and pinned or otherwise clamped in place.

A puncture test program, also referred to as a data acquisition program, is run and the puncture test is initiated at step 350. Programming to collect data from the puncture test is preferably stored on the computer or run from a floppy disc. The programming necessary to conduct the puncture test will be understood by those skilled in the art based on the description of the steps below and the details of the programming are not described in detail herein. The test programming preferably prompts a user to enter a sample can name or number or both at step 352. The name or number previously marked on the sample can is entered at this step. An indication that the user is ready to begin the test is entered in the test program at step 354. Preferably, the program is set-up to accept a keyboard entry or mouse click to run the program to accept data points from the puncture test. Also, the program is preferably set-up to have a time delay, in which the test must be completed before the program resets itself. A 10 second delay is preferred, but other delay increments may be used.

At step 356, the carriage or weight is unpinned or unclamped and the carriage is moved to the desired starting point and released to allow the penetrator to impact the sample can. Alternatively, the carriage may be released directly from its pinned or clamped location, using that location as the starting point. A driving force, preferably a pulley and weight system, moves the carriage and penetrator along the length of the horizontal puncture gauge to impact the sample can. The test is completed in a few seconds.

The data acquisition programming preferably collects data points for displacement, load, and elapsed time during the test. Additionally, data on the internal pressure of the sample can during the impact event may also be collected.

Preferably, data acquisition programming collects, converts, and records a set number of data points from each sensor used on the puncture gauge at step 358. It is preferred that data from at least a displacement transducer, a load cell, and elapsed time be collected. Other data points, such as internal pressure of the sample can during the impact event, may also be collected in accordance with the invention with the addition of the appropriate sensors to the puncture gauge.

The types of sensors used in instrumented impact testing, including those described for the horizontal puncture gauge of the present invention, are capable of being sampled hundreds of thousands of times per second. This type of sampling frequency is not necessary to obtain meaningful data from a puncture test. Therefore, it is preferred according to the present invention to vary the sample frequency so that approximately 1000 data points are collected for each sensor during a test. Other sample frequencies may be used according to the invention. The sample frequency is generally set before the test begins, but the data acquisition programming may be modified to allow entry of different sample frequencies for each test.

Step 358 preferably includes a delay in recording data points during a test. The delay is most preferably triggered by voltage readings from various sensors, but may also be a time delay. In the preferred method, the computer begins recording data when the displacement transducer reaches a predetermined voltage, generally of approximately 0.8 volts. The data is initially recorded as a voltage reading and is then converted to engineering units, depending on the particular parameter. Conversion of voltage readings to engineering units is well known in the art. It is preferred that the data acquisition program eliminate unessential data points from the beginning and end of the test.

The test is complete and the data collected during the puncture test is preferably analyzed by the data acquisition programming at step 360. Once the test is completed, the test programming preferably prompts the user to enter a file name, at step 362, to save the test data from step 358. Alternatively, step 352 may be skipped and the sample name and/or number entered as the file name at step 362. Another alternative includes entering the sample name and/or number at both step 352 and 362.

Once the data is collected from the puncture test, and preferably stored in the memory of the computer or on a floppy disc, the data acquisition program begins analysis of the data at step 364. The analysis is generally started by splitting or grouping the data according to the type of measurement, such as load, displacement, and elapsed time. It is preferred that in the analysis of the data, the data acquisition programming include a filter to reduce the amount of high frequency noise in the data due to analog to digital conversion; however, a filter is not required. The filter calculates the median of a predetermined number of data points before and after each entry and replaces that entry with the median value. According to the present invention a filter using approximately 20 data points before and after each data entry (a rank of 20) achieves the best results. A rank lower than 20 results in unnecessarily noisy data, while a rank greater than 20 artificially shrinks the magnitude of the results.

Data acquisition programming also preferably has the capability to generate results for various data queries at step 366. These queries may include identification of maximum load, maximum deflection or displacement, deflection at maximum load, energy absorbed, and graphical representations of load and deflection over time. Additionally, it is preferred that the data acquisition programming be capable of statistical analysis of the data collected. These queries may be pre-set to automatically be generated, or may be generated by user prompt. Determination of maximum values is simply found by searching the filtered data, or unfiltered data if such data is used, for the maximum value recorded. Determination of the deflection at maximum load is calculated by the data acquisition programming by taking the difference between the deflection data point when the penetrator makes contact with the sample can (when the load begins to increase) and the deflection data point when the maximum load occurs. The energy absorbed during the impact event is simply a numerical integration of the load versus deflection history. Data acquisition programming is also preferably capable of generating graphical representations of the data collected. The calculations needed to complete the analysis step are well known in the art.

According to the present invention, it is also preferred to periodically check the repeatability of the horizontal puncture gauge by testing a batch of baseline aluminum cans. Periodic repeatability testing of step 370 ensures that the puncture gauge is performing according to its specifications and that the test results demonstrate a state of statistical control. As previously described, repeatability is a key characteristic of any instrumented impact testing device. Repeatability testing should be carried out at a set frequency of testing sessions or a set time period, generally on a whichever comes first basis. Applicants prefer to conduct repeatability testing after approximately 100 puncture tests or after the gauge has been in use for about a week, whichever occurs first. Other frequencies may be used in accordance with the invention.

Step 372 includes preparing baseline containers, or cans, for testing. The baseline containers should be of the same design and preferably sampled from a single run from a specific bodymaker to reduce container variation as much as possible. Prior to using the gauge for any experimental purposes, it is desirable to verify the repeatability of the gauge by determining the control limits using a homogeneous set of samples. It is desirable to obtain at least 100 containers from the same line, run, and bodymaker to conduct the state-of-control tests. More cans may be obtained, or fewer cans may be obtained, although fewer cans results in fewer data points to track the repeatability of the gauge. It is preferred to average the results of 4 cans to establish one data point on the control chart, so a batch of 100 cans results in 25 data points. Once a statistical state-of-control is achieved for the gauge, experimental testing employing cans of various attributes may begin. At regular intervals (100 cans tested, or 1 week in service, whichever comes first), the gauge testing parameters should be set-up to their default settings (described below) and cans from the baseline lot (the lot used to establish the control limits) should be punctured to ensure that the results still indicate that the gauge is operating in a state-of-control. A minimum of 4 cans (i.e. single data point) should be used. If an out-of-control indication is received, based on the results of the data when added to the control chart, the gauge operator should investigate to determine the cause of the out-of-control condition, and make alterations to the gauge to return it to a state of statistical control (verified by additional points on the control charts).

For the purposes of control charting, it is important to continue to control chart using the same homogeneous batch. If a new baseline needs to be established, a new set of 100 cans (i.e. 25 data points) is required to establish new control limits, which may differ from the previous control limits due to differences between the cans used to set those limits. The baseline containers are prepared for testing in the same manner described above for regular puncture tests. The baseline containers are preferably filled with approximately 355 mL of water, sealed and pressurized to 55 psi, placed in position in the puncture gauge with the impact area with cleaned and degreased. Step 374 includes preparing the puncture gauge, including running the appropriate checks, starting the data acquisition system, and running the test as described above for regular tests. Puncture gauge testing parameters need to be consistent for all baseline testing performed. The Applicants prefer using a hemispherical tipped penetrator with a 0.250 inch diameter tip, an impact velocity of approximately 6.5 feet/second and a can internal pressure of 55 psi on a 355 mL fill.

Data from the baseline tests are calculated and analyzed at step 376. It is preferred that the individual maximum load, deflection, and energy from each baseline sample be averaged together. The average values are entered into a baseline control chart for monitoring the repeatability of the puncture gauge. It is preferred that the data acquisition programming calculate and chart the average test results and the values for upper and lower control limits based on 3 standard deviations. The control charts generated are valuable in tracking the long-term output of the gauge. They may be used to spot equipment calibration problems, as well as possible mechanical problems with the gauge, such as poor alignment. It is important to catch these types of problems early to avoid wasting valuable or hard-to-obtain test specimens (particularly for experimental can designs) and to avoid reporting of erroneous results. Maintaining proper calibration of the gauge is also important for accurate and repeatable comparisons between old and new test results.

In the event a baseline or regular puncture test results in data that appears erroneous or no data is collected at all, a troubleshooting step 380 may be performed. If the system is not acquiring data from a test run, then the following are some checks that may be conducted at step 382. All wire connections may be checked and replaced or reconnected if necessary. The data acquisition system may need to be rebooted. The sample frequency set in the data acquisition system may need to be adjusted. If the system is acquiring out of tolerance or otherwise erroneous appearing data from a regular or baseline test, then the following are some checks that may be conducted at step 384. The data acquisition system may need to be rebooted. The calibration checks for the sensors may need to be re-run and the appropriate calibration carried out. Multiple baseline groups may be tested to determine whether lack of control is repeatable and to determine which data channel, such as the displacement transducer or load cell, is producing the erroneous data. Sensors may be replaced.

A horizontal puncture gauge and method of operation are described according to the invention. It will be understood by those of skill in the art that variations in the components or arrangement of components described may be made within the scope of the invention. Additionally, variations in the steps of the method described may be made within the scope of the invention.

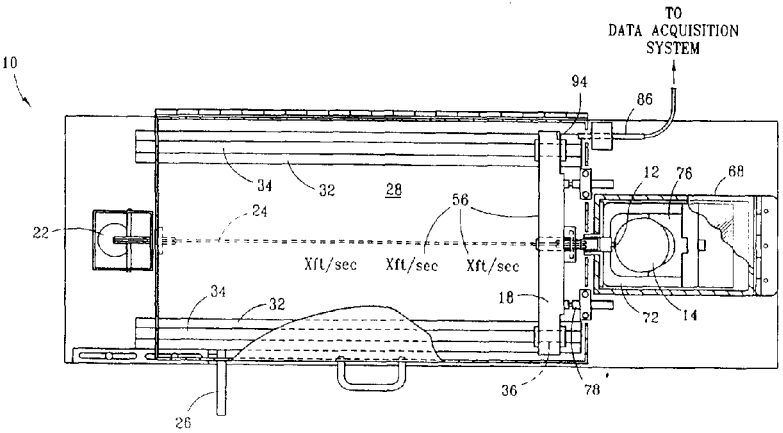

What is claimed is:

1. An apparatus for conducting impact tests on an aluminum beverage can comprising:

an aluminum can in an upright position;

a penetrator to impact the aluminum can;

a penetrator driving mechanism to move the penetrator horizontally from a starting position to a position of impact with the aluminum can; and at least one sensor to measure data from the impact of the penetrator and the aluminum can.

2. The apparatus of claim 1 further comprising:

a carriage to support the penetrator;

a base plate supporting the carriage and the aluminum can; and a data acquisition system for compiling and converting data from at least one sensor.

3. The apparatus of claim 2 further comprising:

a housing surrounding the aluminum can to contain liquid spray upon puncture;

an opening to allow the liquid spray to drain;

a support to maintain the aluminum can in an upright position; and at least one shock absorber to prevent the carriage from impacting the housing.

4. The apparatus of claim 3 wherein the housing includes a penetrator opening to allow the penetrator to impact the aluminum can.

5. The apparatus of claim 2 wherein the base plate further comprises a track along which the carriage is driven toward the aluminum can.

6. The apparatus of claim 2 wherein there are two sensors comprising a load cell and a displacement transducer and wherein the load cell is mounted on the carriage and the displacement transducer is located on the base plate near the aluminum can.

7. The apparatus of claim 6 wherein the displacement transducer includes a target mirror located on the carriage.

8. The apparatus of claim 6 wherein the penetrator is attached to the load cell.

9. The apparatus of claim 6 further comprising a cover over the base plate.

10. The apparatus of claim 1 wherein the penetrator driving mechanism comprises:

a weight; and a tow cable connected to the weight and to the penetrator.

11. The apparatus of claim 10 wherein the tow cable is connected to the penetrator and the weight via at least one pulley.

12. The apparatus of claim 10 further comprising a carriage to support the penetrator and wherein the tow cable is connected to the carriage and the weight via at least one pulley.

13. The apparatus of claim 10 further comprising a weight tower, wherein the weight tower comprises:

an enclosure housing the weight; and a base to support the weight in a fallen position.

14. The apparatus of claim 1 wherein there are two sensors comprising a load cell and a displacement transducer.

15. The apparatus of claim 1 wherein the aluminum can contains liquid and is pressurized and wherein the penetrator impacts the can in an area below the surface of the liquid.

16. A horizontal puncture gauge apparatus comprising:

a sample container;

a base plate supporting the sample container;

at least one rail attached to the base plate;

a penetrator supported by a carriage for movement along the rail toward the sample container;

a penetrator driving mechanism to move the carriage horizontally;

a load cell attached to the penetrator;

a displacement transducer; and a data acquisition system for collecting and analyzing data from the load cell and displacement transducer.

17. The apparatus of claim 16 further comprising:

a support for the sample container;

a target mirror for the displacement transducer;

a release lever for securing and releasing the carriage from an initial position; and a splash chamber around the sample container.

18. The apparatus of claim 17 wherein the splash chamber comprises:

an opening for the penetrator; and a drain opening.

19. The apparatus of claim 18 wherein the base plate includes an opening corresponding to the drain opening in the splash chamber.

20. The apparatus of claim 17 wherein the penetrator driving mechanism comprises:

a weight;

a tow cable connected to the weight and the carriage; and at least one pulley over which the tow cable moves.

21. The apparatus of claim 20 wherein the release lever is a pin to secure the carriage in an initial position along the base plate.

22. The apparatus of claim 20 wherein the release lever is a pin to secure the weight in an initial position.

23. The apparatus of claim 20 further comprising a housing for the weight.

24. The apparatus of claim 23 wherein said housing comprises a base to support the weight in a fallen position and wherein the housing provides support for a pulley.

25. The apparatus of claim 16 wherein the sample container is an aluminum can that contains liquid and is pressurized.

26. The apparatus of claim 25 wherein the aluminum can is in an upright position and impacted in a thinwall region.

27. The apparatus of claim 25 wherein the aluminum can is resting on its sidewall and impacted in an end region.

28. The apparatus of claim 16 wherein the penetrator driving mechanism comprises:

a weight;

a tow cable connected to the weight and the carriage; and at least one pulley over which the tow cable moves.

29. The apparatus of claim 16 wherein the data acquisition system comprises:

a data acquisition card connected to the load cell and displacement transducer;

a computer connected to the data acquisition card; and a program for analyzing data collected from the load cell and displacement transducer.

30. The apparatus of claim 16 further comprising:

a support leg for the base plate;

a drain opening in the base plate; and a catch basin located under the drain opening.

31. The apparatus of claim 16 further comprising:

a shock absorber located in front of the sample container wherein the shock absorber permits the penetrator to impact the sample container without the carriage impacting the sample container.

32. A horizontal puncture gauge apparatus for impact testing of aluminum cans comprising:

a sample aluminum can in an upright position;

a penetrator for movement in a horizontal direction to impact the aluminum can; and a sensor for measuring data during impact.

33. The apparatus of claim 32 wherein the penetrator is moved by force of gravity.

34. The apparatus of claim 32 wherein the sensor is a load cell.

35. The apparatus of claim 32 wherein the sensor is a displacement transducer.

36. The apparatus of claim 32 further comprising:

a carriage supporting the penetrator;

a track along which the carriage moves horizontally toward the sample can; and a shock absorber.

37. The apparatus of claim 36 wherein the carriage includes bearings for movement along the track.

38. The apparatus of claim 36 wherein the shock absorber allows the penetrator to impact the sample can without allowing the carriage to impact the sample can.

39. The apparatus of claim 32 further comprising:

a data acquisition card connected to the sensor;

a computer connected to the data acquisition card; and programming for analysis of data collected from the sensor.

40. A method of testing puncture resistance in an aluminum can with a horizontal puncture gauge comprising:

providing a sample aluminum can in an upright position;

preparing a data acquisition system to collect data;

releasing a penetrator from a starting position to impact the sample can; and collecting data from the impact.

41. The method of claim 40 wherein the step of providing a sample aluminum can comprises:

providing an aluminum can containing liquid;

sealing and pressurizing the aluminum can;

cleaning the area of impact on the aluminum can to remove dirt and grease;

placing the aluminum can in an upright position in the horizontal puncture gauge.

42. The method of claim 41 wherein the step of providing a sample aluminum can further comprises marking the aluminum can with a rolling direction of the aluminum alloy coil stock from which it was made.

43. The method of claim 42 further comprising marking the aluminum can with an identification label.

44. The method of claim 40 wherein the step of preparing a data acquisition system comprises:

starting a computer and a sensor; and running a self-calibration utility for a data acquisition board or a data acquisition card.

45. The method of claim 44 further comprising allowing the computer and sensor to warm-up about 15 minutes before testing.

46. The method of claim 44 wherein the sensor is a displacement transducer and wherein the horizontal puncture gauge comprises a carriage supporting a penetrator and a shock absorber that permits the penetrator to impact the sample can but prevents the carriage from impacting the sample can.

47. The method of claim 46 further comprising:

running a displacement transducer check utility comprising pushing the carriage against the shock absorbers until a maximum reading is obtained; and adjusting the fine gain of the displacement transducer until a voltage reading of about 5 volts is obtained.

48. The method of claim 47 wherein the fine gain is adjusted by adjusting a screw on the displacement transducer.

49. The method of claim 40 wherein the horizontal puncture gauge comprises a pin to secure a carriage supporting the penetrator in the starting position and wherein the step of releasing the penetrator comprises unpinning the carriage.

50. The method of claim 40 wherein the horizontal puncture gauge comprises
- a pin to secure a carriage supporting the penetrator in a position beyond the starting position and wherein the step of releasing the penetrator comprises:
  - unpinning the carriage;
  - moving the carriage to the desired starting point; and
  - removing the force holding the carriage in the starting position.

51. The method of claim 40 wherein the step of collecting the data comprises:

converting a voltage reading from a sensor to engineering units;

transferring the data to a computer; and storing the data.

52. The method of claim 51 wherein the data is stored in memory on a computer or on a floppy disk.

53. The method of claim 40 further comprising analyzing the data collected.

54. The method of claim 53 wherein the step of analyzing comprises:

identifying maximum values for data; and generating graphical representations of the data.

55. The method of claim 54 further comprising generating statistical information on the data.

* * * * *

UNITED STATES PATENT AND TRADEMARK OFFICE
CERTIFICATE OF CORRECTION

PATENT NO. : 6,505,499 B1
DATED : January 14, 2003
INVENTOR(S) : Hackworth et al.

It is certified that error appears in the above-identified patent and that said Letters Patent is hereby corrected as shown below:

Please replace Title page with the attached Title page.

<u>Drawings,</u>
Please replace informal Figures 1 and 2 (Sheets 1 of 5 and 2 of 5) with the attached numbered formal drawing sheets.

Signed and Sealed this

Seventeenth Day of August, 2004

JON W. DUDAS
*Acting Director of the United States Patent and Trademark Office*

United States Patent
Hackworth et al.

(10) Patent No.: US 6,505,499 B1
(45) Date of Patent: Jan. 14, 2003

(54) PUNCTURE RESISTANCE IN ULTRA-THIN ALUMINUM PRESSURE VESSELS

(75) Inventors: Matthew R. Hackworth, Pearland, TX (US); John W. Cooley, Ballwin, MO (US); John M. Henshaw, Tulsa, OK (US); Randy Houchins, St. Louis, MO (US); Paul Siefken, O'Fallon, MO (US); Dwight Davis, Tulsa, OK (US)

(73) Assignee: Metal Container Corporation, St. Louis, MO (US)

(*) Notice: Subject to any disclaimer, the term of this patent is extended or adjusted under 35 U.S.C. 154(b) by 0 days.

(21) Appl. No.: 09/821,890

(22) Filed: Mar. 30, 2001

Related U.S. Application Data

(60) Provisional application No. 60/193,596, filed on Mar. 30, 2000.

(51) Int. Cl.[7] ............................... G01M 3/02
(52) U.S. Cl. ........................... 73/12.09; 73/52
(58) Field of Search ................. 73/12.01, 12.04–12.07, 73/12.09, 12.11–12.14, 818, 821, 52, 838, 839

(56) References Cited

U.S. PATENT DOCUMENTS

| | | | |
|---|---|---|---|
| 2,645,936 A | * 7/1953 | Albrrecht | 73/821 |
| 4,555,935 A | * 12/1985 | Elert | 73/52 |
| 4,721,000 A | 1/1988 | Scanlon | 73/833 |
| 5,567,866 A | 10/1996 | Popp | 73/11.09 |
| 5,616,857 A | 4/1997 | Merck, Jr. et al. | 73/82 |
| 5,929,348 A | * 7/1999 | Stein et al. | 73/12.07 |

OTHER PUBLICATIONS

*Drop and Puncture Testing of 1/4 Scale Model of NUPAC 125B Rail Cask*, M.M. Warrant and B.J. Joseph, Sandia National Laboratories, Albuquerque, NM 87185, pp 357–362, no date.

*Standards for High Pressure Cylinders for the On–Board Storage of Natural Gas as Fuel for Automotive Vehicles*; Joe Wong and Craig Webster, International Conference on Pressure Vessel Technology, vol. 2, ASME 1996: pp 287–292, Jul. 21–26, 1996.

*Static and Dynamic Penetration of Steel Tubes by Hemispherically Nosed Punches*: g. G. Corbett, et al. Int. J. Impact Engineering; vol. 9, No. 2, pp 165–190, Great Britain, 1990.

*On the Catastrophic Failure of High–Pressure Vessels by Projectile Impact*, Z. Rosenberg, et al., Int. J. Impact Engineering, vol. 15, No. 6, pp 827–831, Great Britain, Feb. 1994.

*Numerical Simulations of Fragment Impact on Liquid Filled Containers*, P.W. Randles, et al., PVP, vol. 361, Structures Under Extreme Loading Conditions, ASME 1998.

*Space Station Jem Design Implementation and Testing for Orbital Debris Protection*; Kuniaki Shiraki, et al., Int. J. Impact Engineering, vol. 20, pp 723–732, Great Britain, 1997.

*Spherical Missile Impact and Perforation of Filled Steel Tubes*; ma Xiaoping, et al., Int. J. Impact Engineering, vol. 3, No. 1, pp 1–16, Great Britain 1985.

(List continued on next page.)

Primary Examiner—Robert Raevis
(74) Attorney, Agent, or Firm—Storm & Hemingway, L.L.P.

(57) ABSTRACT

An apparatus and method for measuring the puncture resistance of an aluminum can that has improved repeatability and more accurately simulates end-use punctures. A penetrator that moves in a horizontal direction and is driven by a falling weight impacts a pressurized aluminum can containing liquid. The aluminum can is impacted by a penetrator of the puncture gauge in an area below the liquid level. Various sensors, such as a load cell and a displacement transducer, measure data from the impact and the data is compiled and analyzed by a data acquisition system.

55 Claims, 5 Drawing Sheets